(12) United States Patent
Dunham et al.

(10) Patent No.: US 7,447,297 B2
(45) Date of Patent: Nov. 4, 2008

(54) X-RAY SOURCE FOCAL SPOT DEFLECTION METHODS AND APPARATUS

(75) Inventors: Bruce Matthew Dunham, Mequon, WI (US); Jonathan Richard Schmidt, Wales, WI (US)

(73) Assignee: General Electric Company, Schenectady, NY (US)

( * ) Notice: Subject to any disclaimer, the term of this patent is extended or adjusted under 35 U.S.C. 154(b) by 55 days.

(21) Appl. No.: 11/499,612

(22) Filed: Aug. 4, 2006

(65) Prior Publication Data
US 2008/0031419 A1    Feb. 7, 2008

(51) Int. Cl.
*H05G 1/52* (2006.01)
(52) U.S. Cl. .................... 378/113; 378/16; 378/137

(58) Field of Classification Search .................. 378/16, 378/19, 113, 137, 138, 208
See application file for complete search history.

(56) References Cited

U.S. PATENT DOCUMENTS

| 4,637,040 | A | 1/1987 | Sohval et al. ............... 378/9 |
| 5,550,889 | A * | 8/1996 | Gard et al. ................. 378/113 |
| 5,898,755 | A | 4/1999 | Meusel et al. .............. 378/137 |
| 6,252,935 | B1 | 6/2001 | Styrnol et al. .............. 378/137 |
| 6,480,572 | B2 | 11/2002 | Harris et al. ................ 378/136 |
| 6,968,039 | B2 | 11/2005 | Lemaitre et al. ............ 378/138 |

* cited by examiner

*Primary Examiner*—Courtney Thomas
(74) *Attorney, Agent, or Firm*—Fisher Patent Group, LLC; Thomas M. Fisher

(57) ABSTRACT

A method includes performing an at least partially automated method to synchronize an x-ray source focal spot (FS) position to a FS deflection feedback signal.

11 Claims, 6 Drawing Sheets

FROM THE PREVIOUS PAGE, WITH THE FS TO THE LEFT, CELL #1 WILL HAVE 0 COUNTS WHILE CELL #6 WILL HAVE FULL COUNTS. WHEN THE FS MOVES TO THE RIGHT, CELL #1 WILL HAVE > 0 COUNTS

X-RAY SOURCE FOCAL SPOT DEFLECTION METHODS AND APPARATUS

BACKGROUND OF THE INVENTION

This invention relates generally to x-ray source focal spot (FS) deflection methods and apparatus, and more particularly to methods and apparatus that provide for synchronization of the switching of the FS position (i.e., focal spot deflection) with a data acquisition system.

Some known systems employ focal spot position switching. For example, see U.S. Pat. No. 4,637,040. For systems employing such FS position switching to increase image resolution, it is desired to synchronize the switching event with the data acquisition system (DAS) so that data is not collected during the transition period. During this transition period, the focal spot size is blurred, causing the image quality to degrade. Therefore, the switching event should not occur during the data collection period, or the image resolution improvements of the FS switching will not be realized.

BRIEF DESCRIPTION OF THE INVENTION

In one aspect, a method is provided. The method includes performing an at least partially automated method to synchronize an x-ray source focal spot (FS) position to a FS deflection feedback signal.

In another aspect, a method includes monitoring an x-ray source deflection synchronization of a system and doing at least one of the following when the system is out of synchronization: a) automatically correcting the synchronization; b) notifying a user; and c) also, if the system is in error, enter the error information into a data stream so that the error can be corrected for in post-processing.

In still another aspect, a system includes an x-ray source, an x-ray detector positioned to receive x-rays emitted from the source, and a computer operationally coupled to the source and the detector. The computer is configured to perform an automated method to synchronize an x-ray source focal spot (FS) position to a DAS timing or other reference timing signal.

In yet another aspect, a computer readable medium is provided that is embedded with a program configured to instruct a computer to synchronize an x-ray source focal spot (FS) deflection to a FS deflection feedback signal.

DETAILED DESCRIPTION OF THE INVENTION

Figure 1:
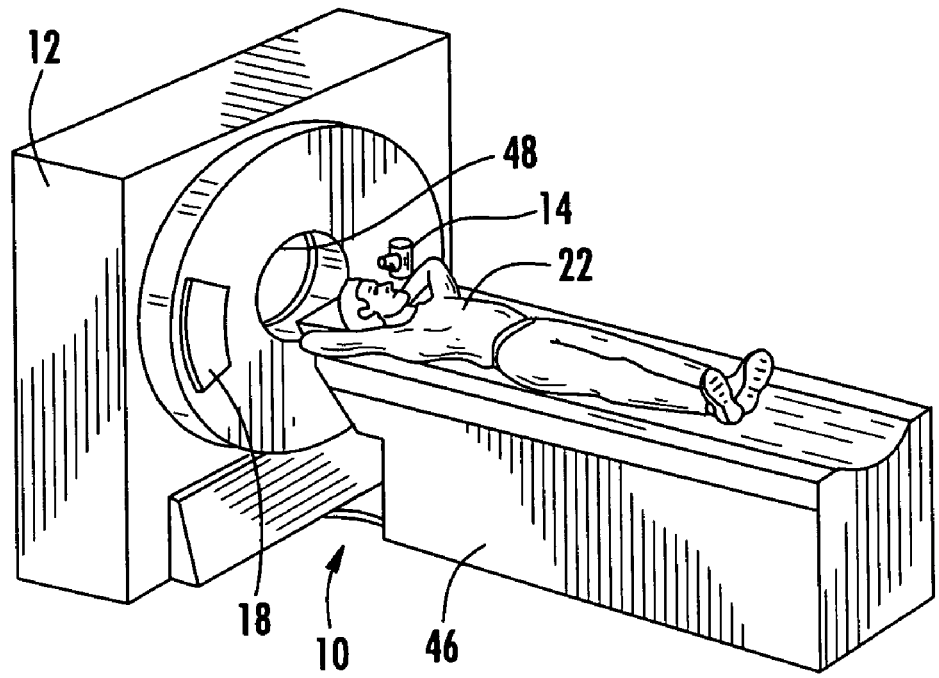
FIG. 1 is a pictorial view of a CT imaging system embodiment.

There are herein described synchronization methods and apparatus useful for imaging systems such as, for example, but not limited to a Computed Tomography (CT) System. The apparatus and methods are illustrated with reference to the figures wherein similar numbers indicate the same elements in all figures. Such figures are intended to be illustrative rather than limiting and are included herewith to facilitate explanation of an exemplary embodiment of the apparatus and methods of the invention. Although, described in the setting of CT, it is contemplated that the benefits of the invention accrue to all system with x-ray sources such as a combined PET/CT system or an x-ray system, and in one embodiment, the system below is a combined PET/CT system.

In some known CT imaging system configurations, a radiation source projects a fan-shaped beam which is collimated to lie within an X-Y plane of a Cartesian coordinate system and generally referred to as an "imaging plane". The radiation beam passes through an object being imaged, such as a patient. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In third generation CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view". A "scan" of the object includes a set of views made at different gantry angles, or view angles, during one revolution of the radiation source and detector.

In an axial scan, the projection data is processed to reconstruct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also, as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image.

Figure 2:
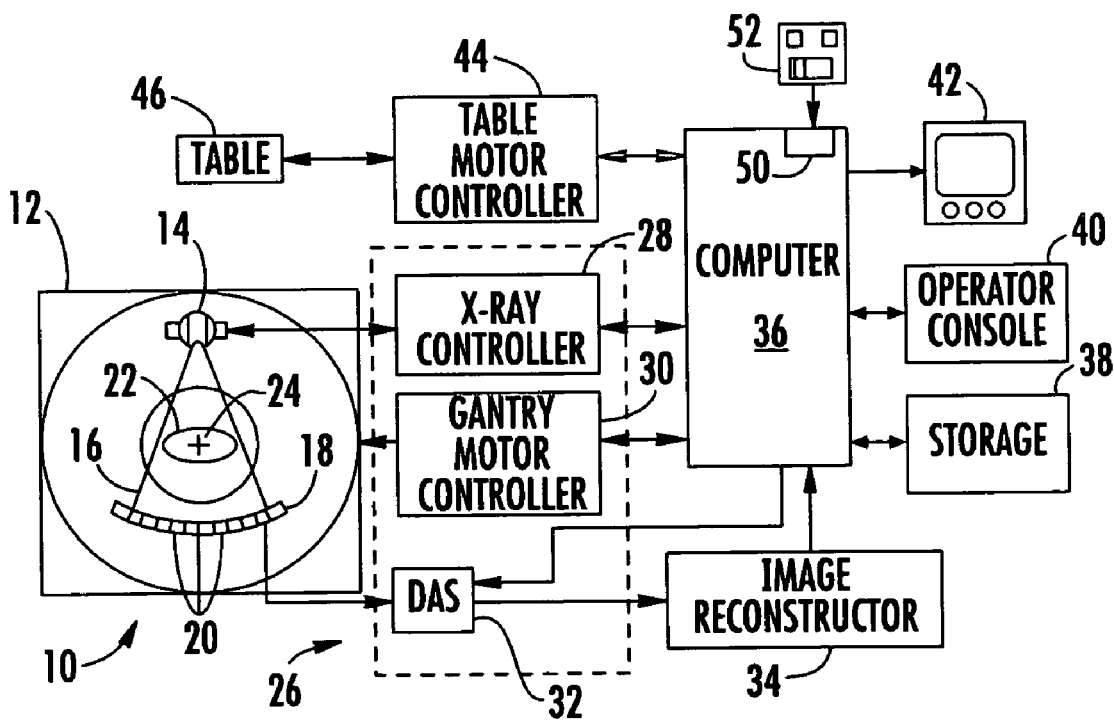
FIG. 2 is a block schematic diagram of the system illustrated in FIG. 1.

FIG. 1 is a pictorial view of a CT imaging system 10. FIG. 2 is a block schematic diagram of system 10 illustrated in FIG. 1. In the exemplary embodiment, a computed tomography (CT) imaging system 10, is shown as including a gantry 12 representative of a "third generation" CT imaging system.

Gantry 12 has a radiation source 14 that projects a cone beam 16 of X-rays toward a detector array 18 on the opposite side of gantry 12.

Detector array 18 is formed by a plurality of detector rows (not shown in FIGS. 1 and 2) including a plurality of detector elements 20 which together sense the projected X-ray beams that pass through an object, such as a medical patient 22. Each detector element 20 produces an electrical signal that represents the intensity of an impinging radiation beam and hence the attenuation of the beam as it passes through object or patient 22. An imaging system 10 having a multislice detector 18 is capable of providing a plurality of images representative of a volume of object 22. Each image of the plurality of images corresponds to a separate "slice" of the volume. The "thickness" or aperture of the slice is dependent upon the thickness of the detector rows.

During a scan to acquire radiation projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of radiation source 14 are governed by a control mechanism 26 of CT system 10. Control mechanism 26 includes a radiation controller 28 that provides power and timing signals to radiation source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized radiation data from DAS 32 and performs high-speed image reconstruction. The reconstructed image is applied as an input to a computer 36 that stores the image in a storage device 38.

Computer 36 also receives commands and scanning parameters from an operator via a console 40 that has a keyboard. An associated cathode ray tube display 42, or LCD display, allows the operator to observe the reconstructed image and other data from computer 36. The operator supplied commands and parameters are used by computer 36 to provide control signals and information to DAS 32, radiation controller 28, and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or an other digital source such as a network or the Internet, as well as yet to be developed digital means. In another embodiment, computer 36 executes instructions stored in firmware (not shown). Generally, a processor in at least one of DAS 32, reconstructor 34, and computer 36 shown in FIG. 2 is programmed to execute the processes described below. Of course, the method is not limited to practice in CT system 10 and can be utilized in connection with many other types and variations of imaging systems. In one embodiment, computer 36 is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits. Although the herein described methods are described in a medical setting, it is contemplated that the benefits of the invention accrue to non-medical imaging systems such as those systems typically employed in an industrial setting or a transportation setting, such as, for example, but not limited to, a baggage scanning CT system for an airport or other transportation center. Although the herein described methods are described in a human patient setting, it is contemplated that the benefits of the invention accrue to non-human imaging systems such as those systems typically employed in small animal research.

The herein described methods and apparatus make use of an x-ray source that has the ability to move the focal spot position in response to an external command, either using a magnetic or electric field. Such a tube is described in U.S. Pat. No. 6,968,039 titled Focal Spot Position Adjustment system for an Imaging Tube. With such a tube, one can take scan data or generate images with the focal spot in slightly different positions, and use the additional data to generate images with higher resolution.

Figure 3:
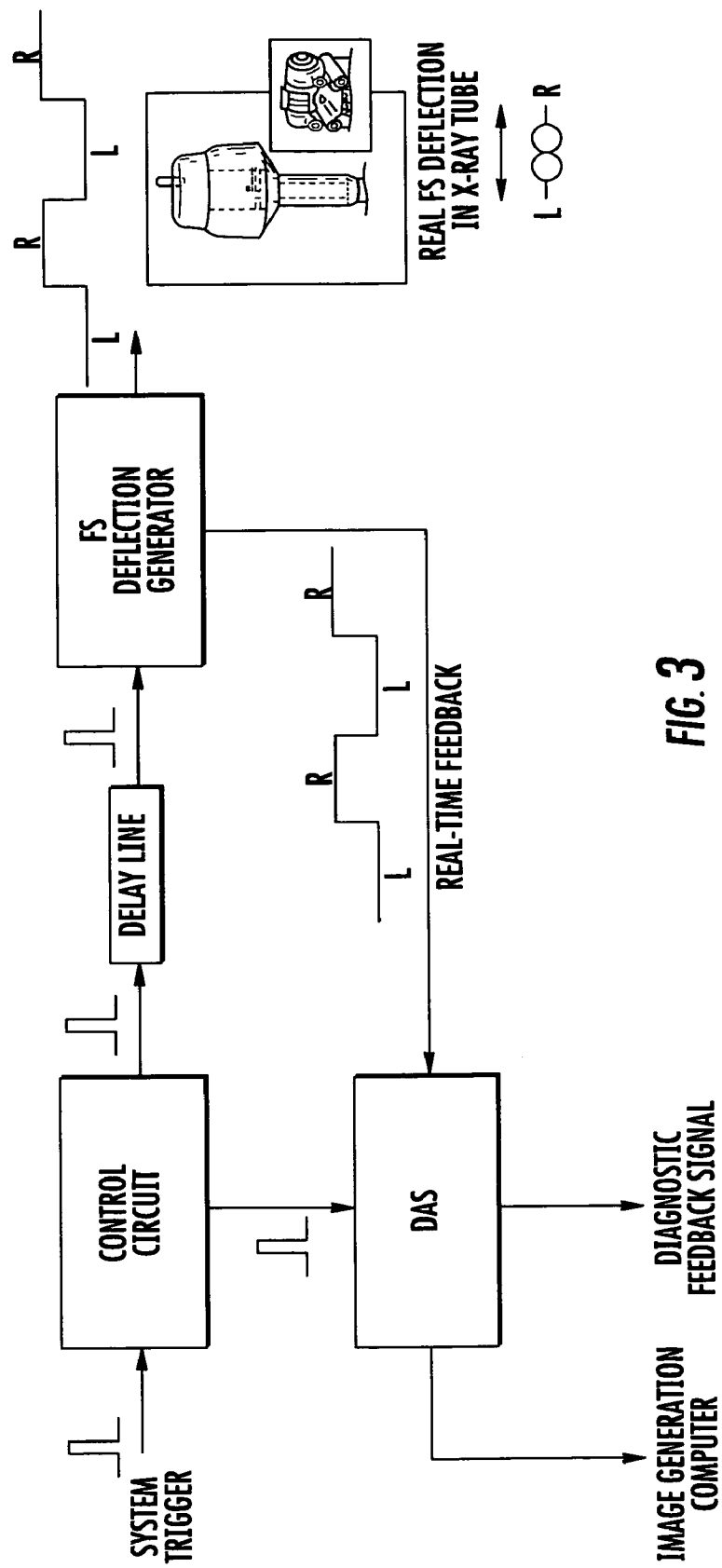
FIG. 3 illustrates delay differences between a DAS and a FS position control.

To work correctly, the spot must switch positions (from right to left, or left to right) at the proper time. If the switching occurs at the wrong time, the spot will move during data collection, effectively blurring out the spot size. One known system sends a trigger to the data acquisition system and an equivalent trigger to the system that controls the focal spot position (in this case, the high voltage generator component). A programmable delay between the trigger generator and the focal spot position control allows one to compensate for communication delay differences between the DAS and the FS position control (see FIG. 3).

Figure 4:
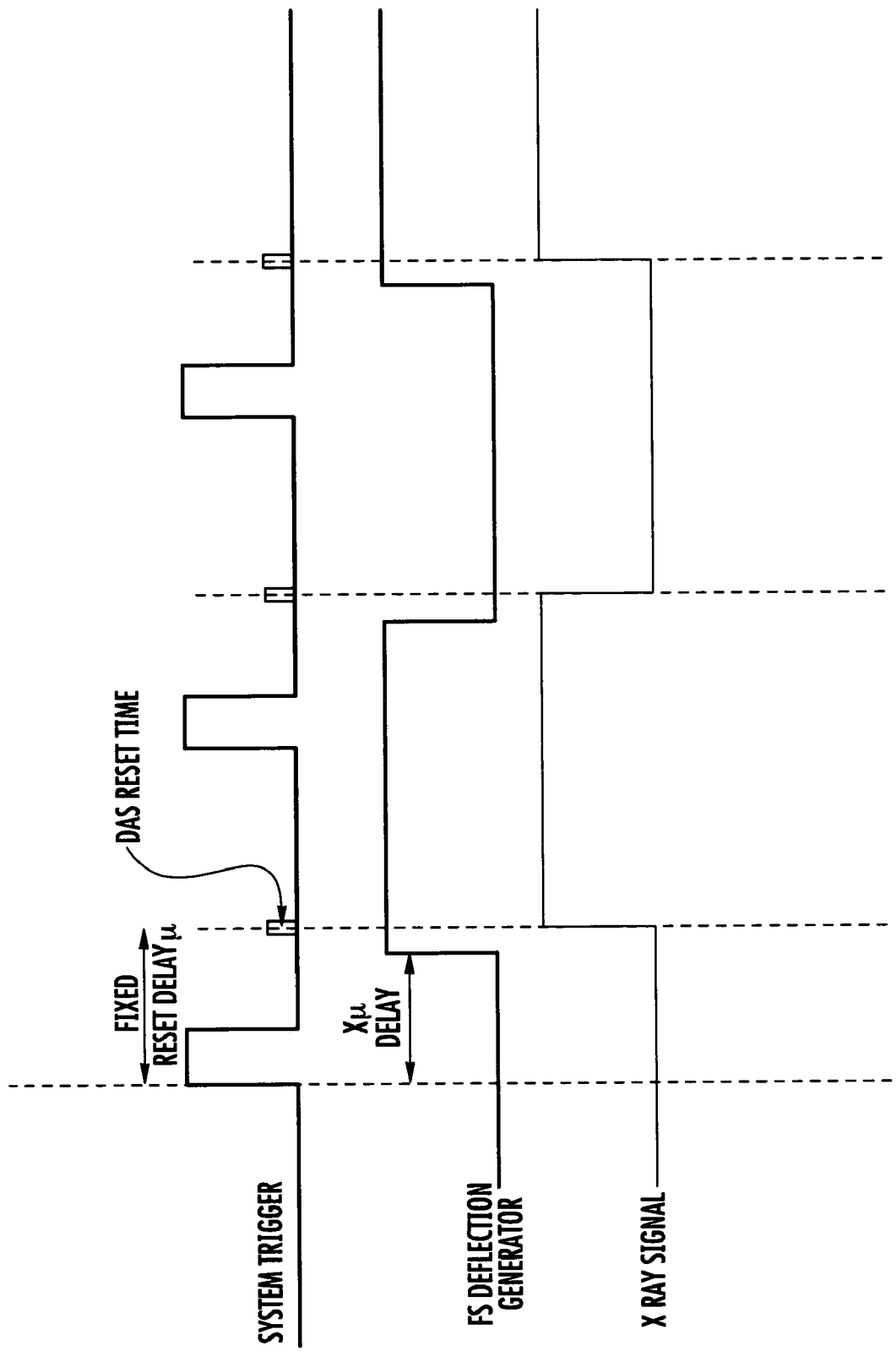
FIG. 4 illustrates a DAS reset time occurrence as a trigger.

Ideally, this delay is set so that the focal spot transition occurs at the same time as the DAS is reset before taking data. The DAS is reset between each view (as stated above, a view is one data collection period, and about 1000 views are collected per gantry rotation) to clear out the previous data before collecting the next view, and this reset time can be from 0 to tens of microseconds. The FS switch time needs to occur during the reset time to avoid blurring of the focal spot within a view, which would reduce image resolution (see timing diagram in FIG. 4). The actual DAS reset time may occur at the trigger, or a known time after the trigger (see 'fixed reset delay' in FIG. 4). The system trigger is the command to do a FS deflection which of course in a real system is delayed.

The herein described methods and apparatus provide a way to determine the correct delay time to use on the scanner, which otherwise is difficult to do. The herein described methods and apparatus will allow an automated means that can be used by a field engineer to calibrate the delay time on the scanner, or a manufacturing technician to set up the initial scanner operation. It is anticipated that the scanner hardware will be stable enough that the delay will not vary much from system to system, but this cannot be guaranteed. In addition, the herein described methods and apparatus provide real-time feedback of the FS location.

Figure 5:
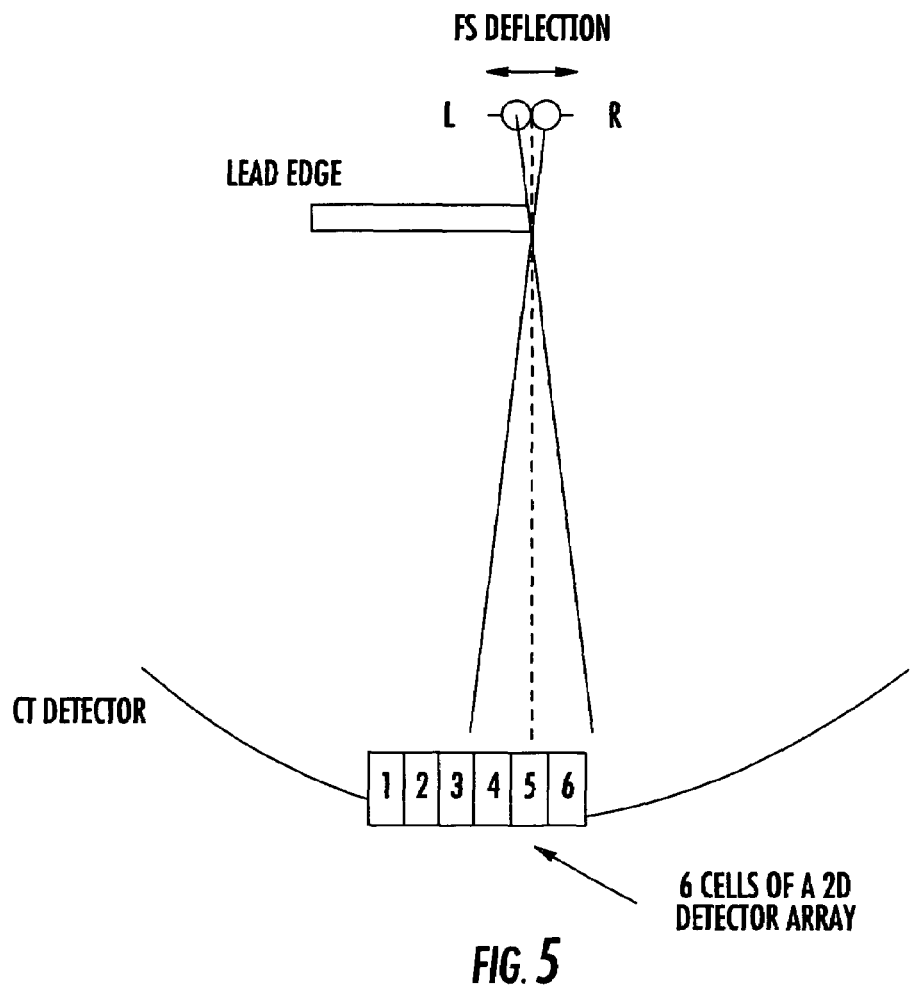
FIG. 5 graphically illustrates a method.
Figure 6:
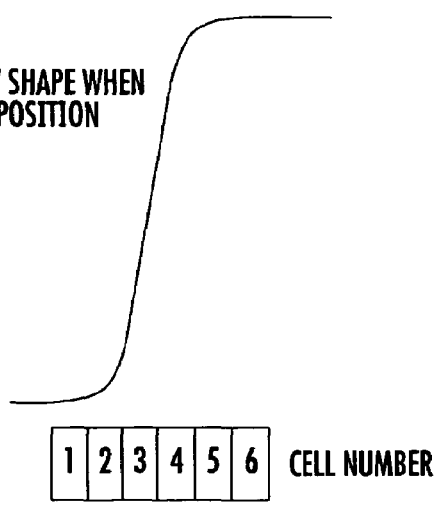
FIG. 6 graphically illustrates a method.

Some herein described methods and apparatus involve placing an x-ray absorbing material (such as a piece of lead) near the beam exit of the x-ray source, or x-ray source collimator and then observing the shadow that falls on the x-ray detector (see FIGS. 5 and 6). The FS is then deflected back and forth, causing the shadow to move on the detector. A particular element on the detector is chosen that is in the shadow (sees no or few x-rays) while the FS is in one position (say the left 'L' position), and is out of the shadow (sees x-rays, and thus generates counts) for the other FS position (say the right 'R' position). The computer control system can then vary the programmable delay until the counts on the detector are minimized when the FS is in the 'L' position. This delay time is then used as a calibration parameter for the system. Note as used herein the term phantom refers to both those objects known in the art as phantoms as well as any object that is highly x-ray absorbing such as a piece of lead.

Figure 7:
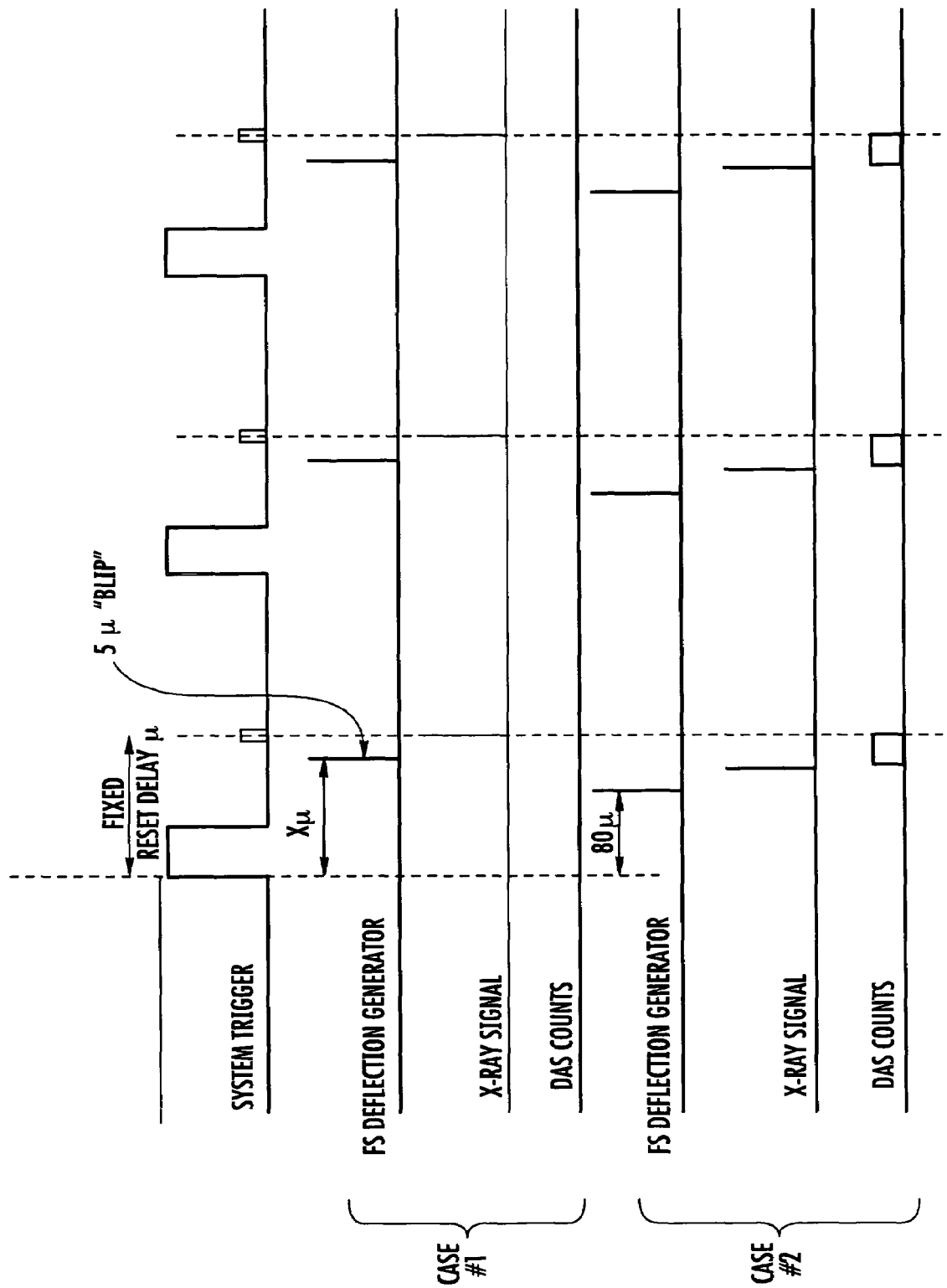
FIG. 7 illustrates two cases.
Figure 8:
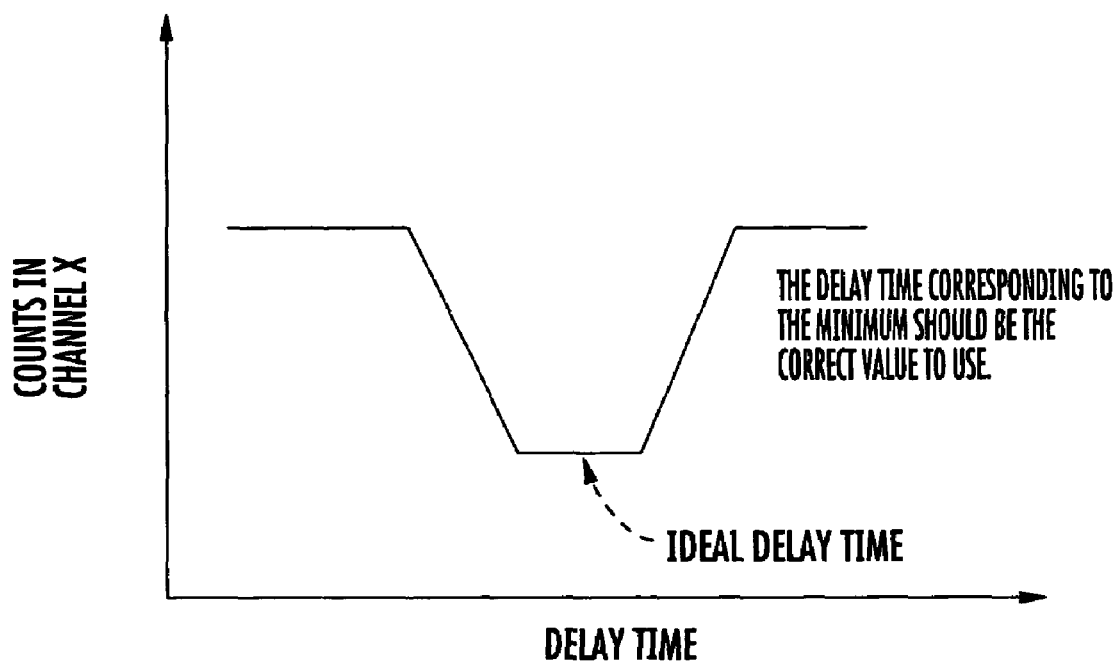
FIG. 8 illustrates delay times.

Due to the very small time window over which the DAS and FS switcher must be synchronized, plus the finite size of the FS, detector, and shadow edge, and bandwidth limitations of the system, other methods may be desirable. In normal operation as described above, the FS is in the L position 50% of the time and in the R position 50% of the time. The dynamic range of the system response can be improved if the timing is adjusted such that the FS in is the R position for only about 5-20 microseconds (the width of the DAS reset time window) and in the L position for the remainder. If the system is perfectly synchronized, then the selected detector channel will never record any counts; that is, the only time x-rays fall on the detector cell, the DAS is in reset mode so records 0 counts, and when the FS is in the L position, the detector cell is in the shadow so still records 0 counts (see FIG. 7, case 1). If the timing is off by more than a few microseconds, the system will start to record counts as the detector will see x-rays at times other than during the reset window (see FIG. 7, case 2). The control system can thus vary the delay time and record the counts, with a graph like FIG. 8. The optimal delay time can easily be determined from the graph.

Once the synchronization is set, it is desirable to monitor this timing to ensure it does not vary. To do this, the system may be provided with a feedback signal representative of the location of the FS—this could be a signal from the x-ray generator or an actual measurement of the FS position using a detector (see FIG. 3). For instance, a signal that is 'high' for the right position, and 'low' for the left position (or the opposite). In one embodiment, the transition timing of the feedback signal with respect to the DAS reset interval could be directly measured digitally by the DAS. In another embodiment the feedback signal could be scaled and low-pass filtered producing an AC waveform at the trigger frequency. This signal when sampled by the DAS A/D (analog to digital converter) will produce an alternating pattern whose value is representative of the phase shift between the reset interval and the original feedback signal. For perfect synchronization, the DAS will generate one value for the 'high' and a different value for the 'low'. Any deviation from this will be an indication of a drift of the synchronization and corrective action can be taken. For example, the view data might look like 1,0,1,0,1,0, ... when perfectly synchronized, and 0.8,0.2,0.8, 0.2, .... when the timing is off. In either case, the measured timing value pattern can be monitored for stability automatically and/or included with the view data for later analysis. Alternatively, the user may be notified by a light or other visual or audible signal. Additionally, the user notification may be by writing to an error log file or any other similar indirect notification as opposed to the light or other direct notification. Note that the including the measured timing value pattern with the view data (i.e., image data) is also an indirect notification. By including the measured timing value pattern along with the image data on a view by view basis, this allows for a retrospective correction when the measured timing value pattern has varied. Additionally, in one embodiment, the timing is automatically corrected and this correction is logged. Therefore, during the retrospective correction step, the computer knows when to stop the correction because the FS deflection is again synchronized.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Technical effects include a reduction in time and simplification of the process of synchronizing the FS switching time with the data acquisition system. Without doing this correctly, the optimal image resolution will not be obtained, and image artifacts may result. In addition, automated real-time monitoring can provide error indication or feedback that the timing is stable. The methods and apparatus described herein could also be used for X-ray systems and baggage scanning systems that use FS deflection for improving resolution. The methods and apparatus described herein could also be applied to systems using magnetic deflection instead of electrostatic deflection.

Exemplary embodiments are described above in detail. The assemblies and methods are not limited to the specific embodiments described herein, but rather, components of each assembly and/or method may be utilized independently and separately from other components described herein.

While the invention has been described in terms of various specific embodiments, those skilled in the art will recognize that the invention can be practiced with modification within the spirit and scope of the claims.

What is claimed is:

1. A method comprising performing an at least partially automated method to synchronize an x-ray source focal spot (FS) position to a FS deflection feedback signal by scanning an x-ray absorbent phantom such that in one FS position substantially all x-rays are absorbed by the phantom and in a second FS position substantially all x-rays impinge a detector.

2. A method in accordance with claim 1 wherein the x-ray source is in a CT system.

3. A method in accordance with claim 1 wherein the x-ray source is in a combination CT/Other modality system.

4. A method in accordance with claim 1 wherein said method further comprises monitoring the synchronization of a system and doing at least one of the following when the system is out of synchronization:
   a) automatically correcting the synchronization; and
   b) notifying a user.

5. A method in accordance with claim 1 further comprising using a DAS to digitally measure the interval between the feedback signal and a DAS reference signal.

6. A method in accordance with claim 1 further comprising scaling and low pass filtering to produce an AC waveform indicative of trigger frequency.

7. A system comprising:
   an x-ray source;
   an x-ray detector positioned to receive x-rays emitted from said source; and
   a computer operationally coupled to said source and said detector, said computer configured to perform an automated method to synchronize an x-ray source focal spot (FS) position to a DAS timing or other reference timing signal, use a DAS to digitally measure an interval between a feedback signal and a DAS reference signal, and scaling and low pass filtering to produce an AC waveform indicative of trigger frequency.

8. A system in accordance with claim 7 wherein said computer configured to receive scan data wherein an x-ray absorbent phantom is scanned such that in one FS position substantially all x-rays are absorbed by the phantom and in a second FS position substantially all x-rays impinge said detector.

9. A system in accordance with claim 7 wherein said computer configured to monitor the x-ray source deflection synchronization of a system and do at least one of the following when the system is out of synchronization:
   a) automatically correct the synchronization;
   b) notify a user; and
   c) also, if the system is in error, enter the error information into a data stream so that the error can be corrected for in post-processing.

10. A computer readable medium embedded with a program configured to instruct a computer to synchronize an x-ray source focal spot (FS) deflection to a FS deflection feedback signal, to use a DAS to digitally measure an interval between a feedback signal and a DAS reset signal, and to perform a scaling and low pass filtering to produce an AC waveform indicative of trigger frequency.

11. A medium in accordance with claim 10 wherein said program further configured to instruct the computer to account for both a FS delay and a DAS delay.

* * * * *